United States Patent [19]

Raulerson

[11] Patent Number: 5,599,311
[45] Date of Patent: Feb. 4, 1997

[54] SUBCUTANEOUS CATHETER STABILIZING DEVICES

[76] Inventor: J. Daniel Raulerson, 1205 Belleville Ave., Brewton, Ala. 36426

[21] Appl. No.: 476,478

[22] Filed: Jun. 7, 1995

Related U.S. Application Data

[62] Division of Ser. No. 280,044, Jul. 25, 1994, Pat. No. 5,509,902.

[51] Int. Cl.⁶ .................................. A61M 5/32; A61F 2/06
[52] U.S. Cl. ............................... 604/175; 623/1; 623/12; 604/174
[58] Field of Search ...................................... 604/174, 175, 604/178, 180; 623/1, 12; 606/194, 195

[56] References Cited

U.S. PATENT DOCUMENTS

| | | | |
|---|---|---|---|
| 1,474,550 | 11/1923 | Philbrook . | |
| 3,574,306 | 4/1971 | Alden | 128/214.4 |
| 4,397,647 | 8/1983 | Gordon | 604/180 |
| 4,435,174 | 3/1984 | Redmond et al. | 604/174 |
| 4,632,670 | 12/1986 | Mueller, Jr. | 604/174 |
| 4,645,492 | 2/1987 | Weeks | 604/174 |
| 4,699,616 | 10/1987 | Nowak et al. | 604/180 |
| 4,723,948 | 2/1988 | Clark et al. | 604/283 |
| 4,942,886 | 7/1990 | Timmons . | |
| 4,981,475 | 1/1991 | Haindl | 604/174 |
| 5,069,206 | 12/1991 | Crosbie . | |
| 5,156,597 | 10/1992 | Verreet et al. | 604/175 |
| 5,215,531 | 6/1993 | Maxson et al. | 604/180 |
| 5,224,935 | 7/1993 | Hollands . | |
| 5,266,073 | 11/1993 | Wall . | |
| 5,267,970 | 12/1993 | Chin et al. . | |
| 5,308,338 | 5/1994 | Helfrich . | |
| 5,368,575 | 11/1994 | Chang . | |
| 5,443,483 | 8/1995 | Kirsch . | |

*Primary Examiner*—Michael J. Milano
*Attorney, Agent, or Firm*—Panitch Schwarze Jacobs & Nadel, P.C.

[57] ABSTRACT

Locatable devices are provided for subcutaneously securing a catheter in an area to be catheterized. In addition, methods for securing a catheter in a subcutaneous location are also provided. In one embodiment, the device comprises two releasably lockable arcuate members interconnected by a hinge. The ends of the arcuate members move with respect to one another from a closed position in which the side surfaces of the arcuate members are coupled in a facing relationship forming a tubular base with a longitudinal passage for receiving a catheter, to an open position in which the ends of the arcuate members are uncoupled and at least partially spaced from each other. Each member is fastened to an end of a connecting material. The connecting material has a length such that it extends within the passage and forms a tightened loop around a catheter inserted within the device. The device may alternatively comprise two tubular members which rotate about each other to create a tightened loop of connecting material around a catheter in a generally cylindrical passage, or an elastic base and a connecting material which forms a loop around a catheter while the base is in a flexed open position and tightens around the catheter while the base is in a relaxed closed position.

5 Claims, 4 Drawing Sheets

SUBCUTANEOUS CATHETER STABILIZING DEVICES

CROSS REFERENCE TO RELATED APPLICATION

This is a division of U.S. patent application Ser. No. 08/280,044, filed Jul. 25, 1994 now U.S. Pat No. 5,509,902.

FIELD OF THE INVENTION

The present invention relates to locatable devices for subcutaneously securing a catheter and methods for subcutaneously securing a catheter with a locatable device which can be located in any stable position for securement.

BACKGROUND OF THE INVENTION

Catheters may be located in various venous locations and cavities throughout the body. Central venous catheters, for example, are placed in four common locations within the chest and/or in the femoral vessels. They may be placed in either the right or left subclavian vein or in the right or left internal jugular vein.

In order to place a catheter in a particular location, a physician uses various techniques. To determine the location of some vessels, for example, a physician may predict the location by physical body landmarks present on the body surface for vessels which are not themselves visible on the body surface. Using landmarks, vessels may be cannulated by first identifying the vessels by aspiration with a long hollow needle. When blood enters a syringe attached to the needle, the syringe is disconnected and a guide wire is passed through the needle into the hollow passage, or lumen, of the vessel. The needle is then removed leaving the guide wire within the vessel. The guide wire projects beyond the surface of the skin.

Several options are then available to a physician for venous catheter placement. The simplest is to pass a catheter into the vessel directly over the guide wire. The guide wire is then removed leaving the catheter in position within the vessel. This technique is typically used when the catheter is of a relatively small diameter, made of a stiff material and not significantly larger than the guide wire. If the catheter is significantly larger than the guide wire, a dilator device is first passed over the guide wire to enlarge the hole following which the catheter is passed over the guide wire and the guide wire removed.

A further option requires an introducer sheath. This is simply a large, stiff thin-walled catheter which serves as a temporary conduit for the permanent catheter which is being placed. The introducer sheath is positioned by placing a dilator device inside of the introducer and passing both the dilator and the introducer together into the vessel. The guide wire and dilator are then removed leaving the thin-walled introducer sheath in place. A catheter such as a Swan-Ganz catheter into which a guide wire cannot be placed or a large silicone catheter such as a Tesio catheter can then be placed through this dilator sheath.

In the case of the Swan-Ganz catheter, the introducer sheath has a hemostasis valve at its proximal end and is simply left in place to function as part of the intravenous system.

In the case of a Tesio catheter, a physician would not leave the stiff, thin-walled catheter in place. Therefore, a straight catheter without a hub or an anchoring device is passed through the sheath and into the vessel. The sheath is removed over the catheter. However, if a hub or any type of anchoring device such as a cuff is permanently attached to the catheter, the sheath must be very large or comprise a tear-away portion which splits into two parts as the sheath is retracted.

Although the larger or the tear-away sheaths work, they are associated with unwanted bleeding and the tear-away sheath tends to pull the catheter out of the vein as the sheath is removed. As a result, there is a need in the art for an anchoring device which can be utilized after the sheath has been removed which enables a physician to use a preferred small diameter, non-tear-away sheath for insertion of certain venous catheters which eliminates the disadvantages associated with large diameter or tear-away sheaths.

A typical anchoring device for these catheters and other venous and body cavity catheters and shunts involves use of a tissue ingrowth cuff fitted on the catheter for stabilization of a catheter in a single position if the catheter is to be left in that position for a significant length of time. Surrounding tissue cells grow into the fabric stabilizing the catheter in a particular location. In using catheters having fabric cuff fittings, it is common to create a subcutaneous tunnel or similar opening several centimeters caudal to the insertion site of the catheter for stabilization of the catheter using the cuff. Subcutaneous tunnels are typically used with insertion of Tesio catheters, for example.

Once the catheter is inserted in a blood vessel or other location, the skin is anaesthetized in a linear fashion for a distance of about 6–8 centimeters caudal to the insertion site. If tunneling is used for venous insertion, a second incision is made and a tunneling device is passed into the incision and out through the skin at the point of catheter insertion creating a subcutaneous tunnel. The catheter is attached to the tunneling device and pulled back through the skin tunnel. A cuff is typically designed to lie in the medial portion of the subcutaneous tunnel. Similarly, when inserting catheters in body cavities and other locations, some catheters are designed such that the cuff is affixed to the catheter in an area which corresponds to a typical area chosen by a physician for subcutaneous securement.

While providing satisfactory anchoring in some situations, catheters manufactured with fabric cuffs already affixed are only available in several set lengths having the cuffs located in areas designed to correspond to average patient sizes. The cuffs are not adjustable to all body sizes and types for optimal positioning. The cuffs are not locatable or movable along the catheter to adjust for placement discrepancies. As most patients vary in size, internal distances involved in subcutaneous placement vary accordingly, deviating from the standard catheter cuff locations commercially available and making stable securement difficult in many cases.

In addition, as the cuff cannot be moved, the physician may have to adjust the catheter itself within the vein to align the cuff within a stable area for securement. Positioning of the catheter is particularly important to proper catheter functioning. For example, if the tip of a central venous catheter is not properly located within a vessel, the catheter may cause the condition of cardiac arrhythmia or otherwise inhibit blood flow. If the catheter tip is not properly located within a body cavity there may not be sufficient access to the tip to allow bodily fluid to properly flow through the catheter.

A need is therefore present for an anchoring device which is locatable within a subcutaneous tunnel or other subcutaneous location for securing a catheter such that the device can be placed by the physician in the most stable position for subcutaneous securement of the catheter without the need to move the catheter itself or to depend upon available commercial sizes of catheters having cuffs already affixed in positions for only average patient sizes. It is also preferable to have an anchoring device which is attachable after insertion of a catheter to obviate the need for large diameter or tear-away sheaths used with certain catheters.

SUMMARY OF THE INVENTION

The present invention comprises a device for subcutaneously securing a catheter in an area to be catheterized. The device comprises a locatable device that includes a first and a second arcuate member. Each arcuate member has an exterior and an interior surface as well as a side surface. The side surface of the first arcuate member is in facing relationship to the side surface of the second arcuate member. A hinge interconnects the first and second arcuate members such that the first arcuate member may move with respect to the second arcuate member between closed and open positions. In the closed position, the side surfaces of the first and second arcuate members are coupled in facing relationship such that a tubular base is formed. The base defines a passage which extends longitudinally through the base for receiving a catheter. In the open position, the first and second arcuate members are uncoupled and at least partially spaced from each other. In addition, the side surfaces of the first and second arcuate members are releasably lockable in the closed position. A connecting material extends within the passage of the device. The connecting material has a first and a second end. The first end is fastened to the first arcuate member, and the second end is fastened to the second arcuate member. The connecting material has a length measured between the first and second ends such that when the first and second arcuate members are in the closed position, the connecting material forms a tightened loop at least partially around the catheter thereby securing the catheter within the device and maintaining free flow of bodily fluid through the catheter.

The present invention also includes a method for subcutaneous securement of a catheter inserted into an area to be catheterized using a device which comprises a locatable device that includes a first and second arcuate member interconnected by a hinge and a connecting material attached at a first end to the first arcuate member and at a second end to the second arcuate member. The method comprises the steps of inserting a distal portion of a catheter into an area to be catheterized. The device is opened such that a space is created between the first and second arcuate members sufficient to receive a catheter. A portion of the catheter proximal the distal portion is inserted through the space such that the proximal portion of the catheter is between the interior surfaces of the first and second arcuate members. The connecting material is between the proximal portion of the catheter and the first and second arcuate members. The device is moved along the proximal portion until the device is positioned in a stable area for securement. The first and second arcuate members are moved about the hinge to a closed position such that the first arcuate member is coupled in facing relationship with the second arcuate member. The connecting material forms a tightened loop around the catheter securing the catheter within the device and maintaining free flow of bodily fluid within the catheter.

In an alternative embodiment, the device of the present invention comprises a first tubular member, a second tubular member, and connecting material. The first tubular member has an exterior surface and an interior surface which defines a passage extending longitudinally through the first tubular member. The second tubular member has an exterior surface and an interior surface which defines a passage extending longitudinally through the second tubular member. At least a portion of the first tubular member is positioned within the passage of the second tubular member such that a space lies between the exterior surface of the first tubular member and the interior surface of the second tubular member. The first tubular member has a hole extending from its exterior to its interior surface. The connecting material is fastened at a first end to the interior surface of the first tubular member. The connecting material has a second end which passes outwardly through the hole and is fastened to the second tubular member. A length of the connecting material within the passage of the first tubular member is formed into a loop, whereby when a catheter is positioned within the loop, the second tubular member is rotated with respect to the first tubular member to pull a portion of the length of the connecting material within the passage of the first tubular member into the space between the members and to tighten the loop around the catheter thereby securing the catheter within the passage of the first tubular member and maintaining free flow of bodily fluid through the catheter.

The present invention also comprises an alternative method for subcutaneous securement of a catheter inserted into an area to be catheterized using a device which comprises a locatable device including first and second tubular members. The first tubular member is positioned within a passage extending longitudinally through the second tubular member. The device comprises a connecting material which has one end fastened to an interior surface of the first tubular member and a second end passing outwardly through a hole in the first tubular member and fastened to the second tubular member. The method comprises the steps of inserting a distal portion of a catheter in an area to be catheterized. A length of connecting material is formed within a passage extending longitudinally through the first tubular member into a loop. A portion of the catheter proximal the distal portion is then inserted through the loop within the passage of the first tubular member. The loop and device are moved along the proximal portion until the device is positioned in a stable area for securement. The second tubular member is rotated with respect to the first tubular member to pull a portion of the length of the connecting material in the passage of the first tubular member into a space between the members to tighten the loop around the catheter thereby securing the catheter within the passage of the first tubular member and maintaining free flow of bodily fluid through the catheter.

The present invention further comprises an alternative embodiment in which the device of the present invention comprises an elastic base having an exterior surface, an interior surface, a first side surface and a second side surface opposite the first side surface. The base is movable from a flexed open position to a relaxed closed tubular position in which the first and second side surfaces are proximate each other, and the base defines a longitudinal passage for receiving a catheter. The device further comprises a first suture hole spaced from the first side surface, and a second suture hole spaced from the second side surface. A connecting material is drawn at a first end through the first suture hole from the interior surface to the exterior surface of the base, and at a second end through the second suture hole from the interior surface to the exterior surface of the base. When the base is in the flexed open position, the catheter is insertable between the interior surface of the base and the connecting material and when the base is in the relaxed closed position, the connecting material forms at least a portion of a loop which at least partially surrounds the catheter. The first and second ends of the connecting material are fastened thereby tightening the connecting material and securing the catheter within the passage of the base while maintaining free flow of bodily fluid through the catheter.

A further alternative method for subcutaneous securement of a catheter inserted into an area to be catheterized is also provided in the present invention. The method uses a locatable device which comprises an elastic base, a first suture hole spaced from the first side surface of the base and a second suture hole spaced from the second side surface of the base. A connecting material is drawn at a first end outwardly through the first suture hole and at a second end outwardly through the second suture hole. The base is movable from a flexed open position to a relaxed closed tubular position. The method comprises the steps of inserting a distal portion of the catheter into the area to be catheterized. The base is moved to and maintained in the flexed open position. A portion of the catheter proximal the distal portion is inserted between the connecting material and the base. At least a portion of a loop which at least partially surrounds the catheter is then formed, and the base is released such that it moves to the relaxed closed position. The first and the second ends of the connecting material are fastened to each other to tighten the connecting material and secure the catheter within the base. The device maintains the free flow of bodily fluid through the catheter.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings, like numerals are used to indicate like elements throughout. In the drawings.

DETAILED DESCRIPTION OF PREFERRED EMBODIMENTS

Certain terminology is used in the following description for convenience only and is not limiting. The words "right," "left," "lower" and "upper" designate directions in the drawings to which reference is made. The words "inwardly" and "outwardly" refer to directions toward and away from, respectively, for example, the metric center of the locatable device and parts thereof. The terminology includes the words above specifically mentioned, derivatives thereof, and words of similar import.

Referring now to the drawings in detail, where like numerals indicate like elements throughout, there are shown in FIGS. 1 through 4, a preferred embodiment of a locatable device for subcutaneous securement of a catheter in an area to be catheterized. Once a catheter is properly inserted in an area to be catheterized, the device, not the catheter, is moved to an optimal location for catheter securement thereby ensuring optimal tip location. In addition, the device is placed on the catheter after insertion enabling large diameter catheters and those having detachable hubs or other attachments to be used in conjunction with small diameter, non-tear-away introducer sheaths.

The device (hereinafter "cuff"), generally designated 10, is comprised of a tubular base 11 and a covering of fabric 12. The tubular base 11, as shown in FIGS. 1–4, includes two interlocking arcuate members 13, 14.

The arcuate members 13, 14 are formed of a biocompatible polymeric material. Preferably, the arcuate members 13, 14 are formed of polyurethane or polypropylene. More preferably, the members 13, 14 are formed of Class 6 biocompatible polypropylene. Other suitable biocompatible polymers for forming the arcuate members 13, 14 include, for example, polyethylene, homopolymers and copolymers of vinyl acetate such as ethylene vinyl acetate copolymer, polyvinylchlorides, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyurethanes, polyvinylpyrrolidone, 2-pyrrolidone, polyacrylonitrile butadiene, polycarbonates, polyamides, fluoropolymers such as polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, polyisobutylene, polymethylstyrene and other similar compounds known to those skilled in the art. It should be understood that this list of possible biocompatible polymers is for exemplary purposes and should not be construed as limiting.

Figures 1, 2:
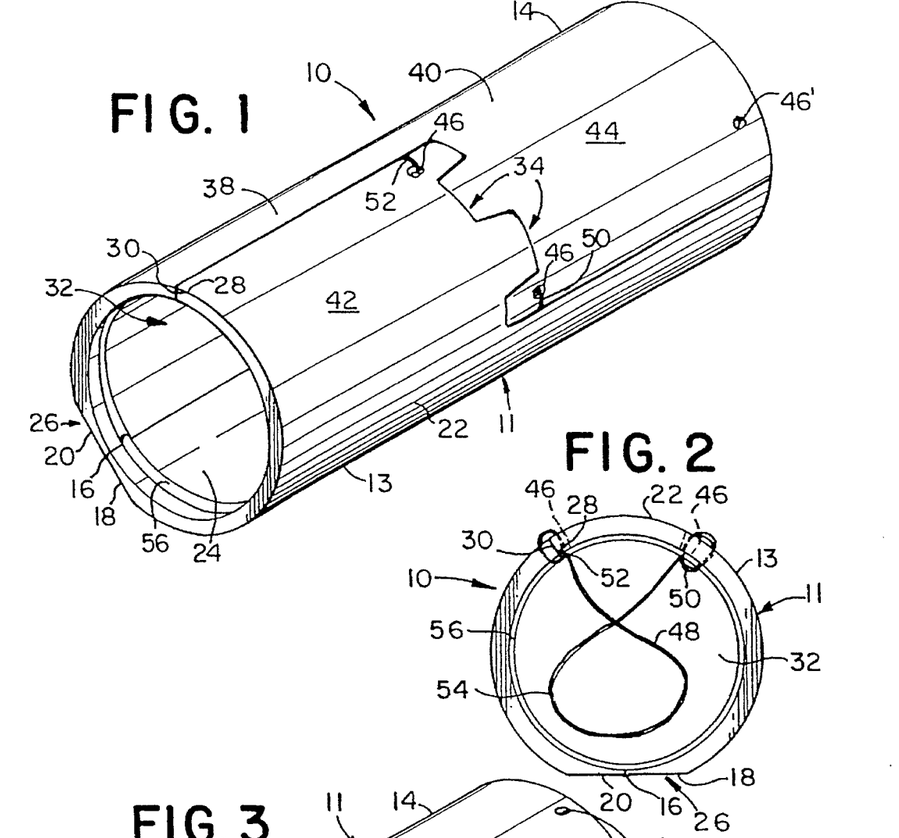
FIG. 1 is a perspective view of a preferred embodiment of a locatable device for subcutaneous securement of a catheter in an area to be catheterized according to the present invention in the closed position.
FIG. 2 is a front elevational view of the device of FIG. 1.
Figure 3:
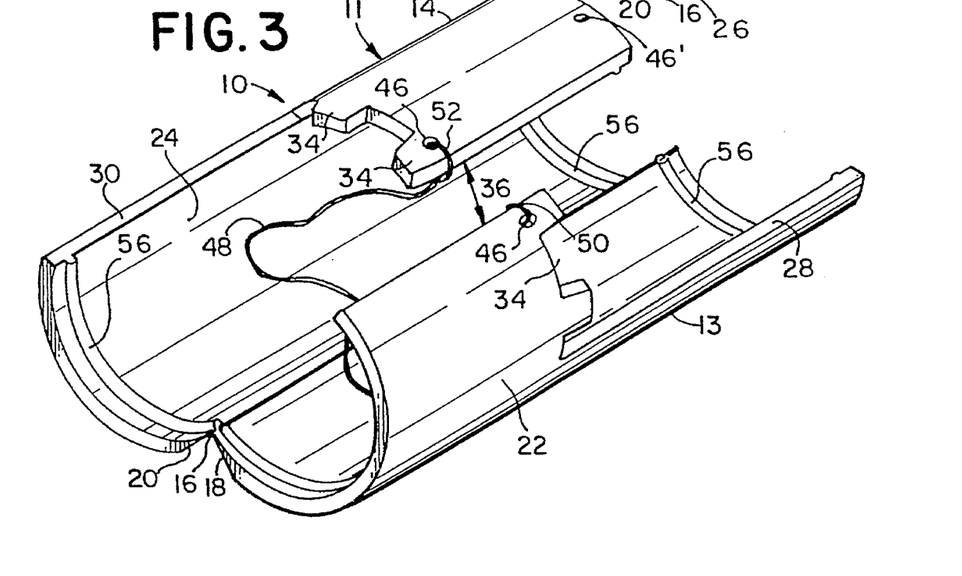
FIG. 3 is a perspective view of the device of FIG. 1 in the open position.
Figure 4:
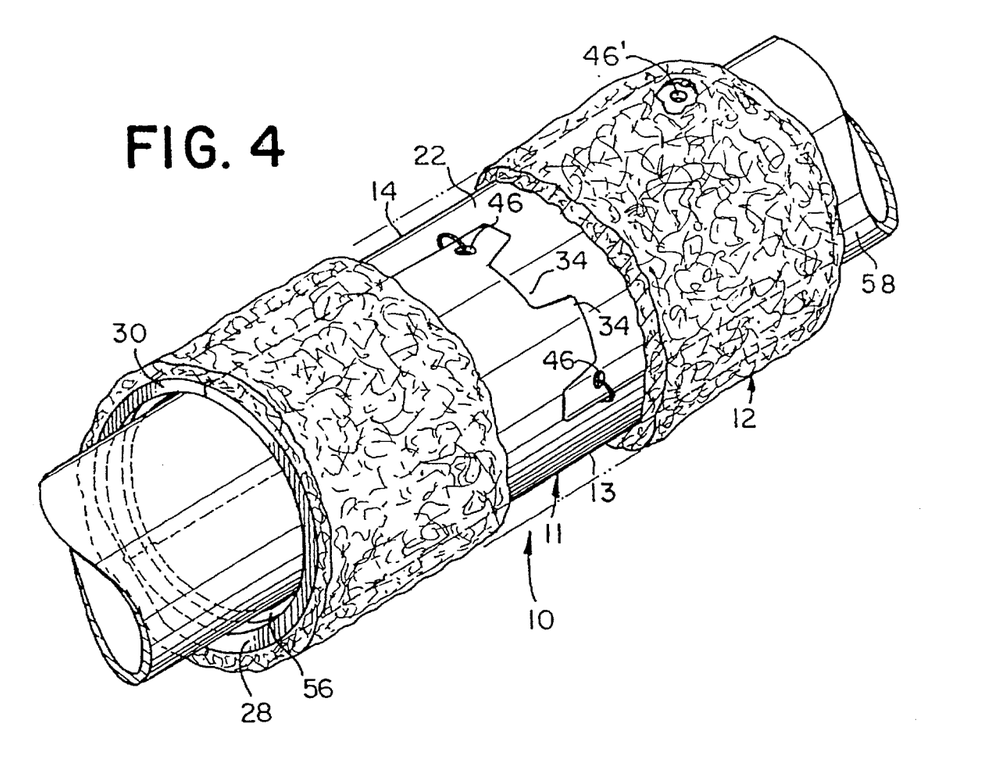
FIG. 4 is a perspective view of the device of FIG. 1 having a fabric covering and enclosed around a catheter.

The arcuate members 13, 14 are interconnected by a hinge 16 such that the first arcuate member 13 is movable with respect to the second arcuate member 14 between a closed position as shown in FIGS. 1, 2 and 4 and an open position as shown in FIG. 3. The hinge 16 is preferably integral with the arcuate members 13, 14, and is formed by tapering the base 11 proximate to one of the side surfaces 18, 20 of each of the members 13, 14. The base 11 is tapered from the exterior surface 22 of the base 11 toward the interior surface 24 of the base 11 proximate the side surfaces 18, 20 along the length of the base 11 such that a generally flat portion 26 is formed on the exterior surface 22 of the base 11 as best shown in FIGS. 1 and 2. At the point where the generally flat portion 26 is thinnest as measured from the exterior surface 22 to the interior surface 24, the base 11 becomes more easily bendable, forming a hinge 16.

The type of hinge 16 provided to the base 11 is not critical to the operation of the cuff 10. While the particular hinge 16 described is the preferred hinge 16, it should be understood by one of ordinary skill in the art from this disclosure that the arcuate members 13, 14 may be joined by other types of hinges without departing from the spirit of the present invention.

When the cuff 10 is in the closed position, the side surfaces 28, 30 of the arcuate members 13, 14 opposite the hinge 16 are coupled in a generally facing relationship such that the base 11 is generally tubular as shown in FIGS. 1 and 4. The base defines a preferably cylindrical passage 32 which extends longitudinally through the base 11 of the cuff 10 in the closed position for receiving a catheter as shown in FIGS. 1 and 2.

When the base 11 of the cuff 10 is in the closed position, the side surfaces 28, 30 of the arcuate members 13, 14 are releasably lockable. In the embodiment shown in FIGS. 1–4, the preferred device for locking the arcuate members 13, 14 in the closed position is to provide the side surfaces 28, 30 of the arcuate members 13, 14 with interlocking segments 34 which snap together by manually forcing the arcuate members 13, 14 into the closed position. The interlocking segments 34 preferably open easily when the arcuate members 13, 14 are pulled apart using a reasonable amount of manual force. More preferably, the interlocking segments 34 and side surfaces 28, 30 are arranged such that the arcuate members 13, 14 overlap. However, it is understood by those of ordinary skill in the art from this disclosure that other locking devices may be used to securely lock the cuff 10 in the closed position, as long as someone operating the cuff 10 is able to easily open it upon application of manual force. Suitable locking devices include, for example, interlocking pieces, a snap-fit device, a slidable locking ring, Velcro®, a latch, a hook and similar locking devices. Preferably the locking device is made from a biocompatible polymeric material such as those described above.

When the base 11 of the cuff 10 is in the open position, the side surfaces 28, 30 of the arcuate members 13, 14 are uncoupled and spaced from each other such that a space 36 is created between the members 13, 14 which is sized to allow a catheter to fit through the space 36 for insertion into the cuff 10.

The side surfaces 28, 30 of the arcuate members 13, 14 may have any configuration as long as they are configured to couple together in the closed position. For example, the side surfaces 28, 30 may extend along the length of the base in a continuous straight line such that each arcuate member 13, 14 has an approximately equivalent generally semi-circular cross section which is constant along the length of the base 11, the cross section taken along a plane perpendicular to the longitudinal axis of the base 11. Alternatively, the side surfaces 28, 30 may, for example, couple along a curved line or a straight line extending at an angle along the length of the base 11 such that the cross section of the arcuate members is not constant along the length of the base 11.

In the embodiment shown in FIGS. 1–4, the side surfaces 28, 30 when coupled preferably extend longitudinally along a generally straight line for approximately one-half of the length of the base 11. The side surfaces 28, 30 are configured on this half 38 of the base 11 such that the cross sections of the arcuate members 13, 14 are constant along the half 38 of the base 11, but the arcuate member 14 has a cross section which is less than a semi-circle and the arcuate member 13 has a cross section which is greater than a semi-circle. Halfway along the length of the base 11, the side surfaces then extend outwardly across a portion of the base 11 forming the interlocking segments 34 shown in FIGS. 1, 3 and 4. After the last interlocking segment 34, the side surfaces 28, 30 then extend along a generally straight line for the remaining half 40 of the base 11. The side surfaces 28, 30 are configured on this half 40 of the base 11 such that the cross sections of the arcuate members 13, 14 are constant along the half 40, but the arcuate member 13 has a cross section which is less than a semi-circle and the arcuate member 14 has a cross section which is greater than a semi-circle. This particular configuration creates overlapping arcuate members 13, 14.

When the side surfaces 28, 30 are configured in the manner shown, the arcuate members 13, 14 have protruding portions 42, 44 extending outwardly from the members 13, 14 which interlock such that the interlocking segments 34 on each arcuate member 13, 14 may lock the cuff 10 in the closed position. A top plan view of this configuration would show protruding members 13, 14 which appear generally L-shaped.

Each arcuate member 13, 14, irrespective of the configuration of the side surfaces 28, 30 preferably has a suture hole 46 which is preferably located proximate to the side surfaces 28, 30. More preferably, the holes 46 are located near the area in which the side surfaces 28, 30 couple when the base 11 is in the closed position. If the edges 28, 30 are configured as shown in FIGS. 1, 3 and 4, the suture holes 46 are preferably located in the protruding portions 42, 44. More preferably, the suture holes 46 are located in the protruding portions 42, 44 proximate to the side surfaces 28, 30 and more preferably near the location in which the protruding portions 42, 44 interlock.

As shown in FIG. 2, the suture holes 46 are preferably tapered such that the diameters of the holes 46 are greater at the exterior surface 22 of the base 11 of the cuff 10 than the diameters of the holes 46 at the interior surface 24 of the base 11 of the cuff 10. The suture holes 46 in the arcuate members 13, 14 proximate to the area in which the arcuate members are coupled preferably serve as an area of attachment for a connecting material 48. A first end 50 of the connecting material 48 is drawn through and tied to the suture hole 46 in one arcuate member 13, and a second end 52 of the connecting material 48 is drawn through and tied to the suture hole 46 in the other arcuate member 14. It should be understood by those skilled in the art from this disclosure that the connecting material 48 can be fastened to the members 13, 14 without using suture holes 46. The purpose of the connecting material 48 is to form a loop 54, preferably an overlapping loop 54, in the cylindrical passage 32 of the base 11 which will tighten around a catheter once the catheter is inserted in the passage 32. The loop 54 should be sufficiently tight around the catheter such that the catheter is secure within the passage 32, but not tight enough to constrict the catheter such that free flow of bodily fluid is maintained once the catheter is secure within the passage 32.

If the side surfaces 28, 30 are configured such that the arcuate members 13, 14 are equal semi-circular members as described above, the length of the connecting material 48 extending within the passage 32 as measured from the first end 50 to the second end 52 may be less than the inner circumference of the base 11. However, the connecting material 48 may be of a longer length and overlapped within the passage 32. In addition, when the base 11 is configured to have protruding interlocking portions 42, 44, the connecting material 48 is preferably of a length which allows for tightening of the loop 54 after the ends 50, 52 of the connecting material 48 have overlapped one another. Overlapping of the loop 54 provides a dynamic tightening capability to the connecting material 48. When overlapped as indicated in FIG. 2, the loop 54 acts in a dynamic ratchet-like manner when tightening around a catheter 58 as shown in FIG. 4.

When the base 11 is open, a catheter is inserted between the arcuate members 13, 14 and on top of the connecting material 48. When the base 11 is closed, the connecting material 48 is looped at least partially, and preferably completely, around the catheter. The connecting material 48 tightens on the catheter within the base 11 and secures it within the passage 32 of the cuff 10. The loop should be tight enough to secure the catheter within the passage 32 while maintaining free flow of bodily fluid through the catheter.

If the side surfaces 28, 30 are configured as shown in FIGS. 1–4, portions of the connecting material 48 near each end 50, 52 should overlap within the passage 32 when the base 11 is in the closed position forming a loop 54 within the passage 32 which tightens at least partially, and preferably completely, around a catheter 58 inserted in the base 11 as shown in FIG. 4. A catheter is inserted in the base 11 while the base 11 is in the open position by positioning it through the space 36. The base 11 is then locked in the closed position and the catheter secured within the tightened loop 54.

The length of the connecting material 48 may be similarly adapted for varying side surface 28, 30 configurations and/or suture hole 46 locations such that regardless of the design, when the catheter is within the passage 32 and the base 11 is closed, the connecting material 48 forms a sufficiently tight loop at least partially, and preferably completely, around the inserted catheter to secure the catheter within the passage 32 of the cuff 10 while maintaining free flow of bodily fluid through the catheter.

The connecting material 48 may be any non-dissolvable, biocompatible material. Suitable non-dissolvable, biocompatible materials include, for example, silk or nylon suture material, braided suture, multi-strand suture, multi-strand braided suture, thread, string and other similar materials. The preferred connecting material 48 is a non-dissolvable suture material. Preferably, the suture material is a 1-0, 2-0, 3-0 or 4-0 non-dissolvable braided suture. Other suitable sutures include, for example, 1-0, 2-0, 3-0 and 4-0 polypropylene braided suture, 1-0, 2-0, 3-0 and 4-0 Prolene monofilament or Epapbond braided synthetic sutures. It is understood by one skilled in the art that any non-dissolvable, biocompatible material may be used without departing from the scope of this invention.

Referring now to FIG. 4, the exterior surface 22 of the base 11 is preferably covered with a layer of fabric 12. The fabric 12 may be adhered to the exterior surface 22 by any suitable biocompatible medical grade adhesive. Preferably, Loctite Brand Medical Grade FMD No. 13 and 14 adhesives are used. However, any biocompatible adhesive is acceptable.

Fabric 12 adhered to the exterior surface 22 functions to promote ingrowth of surrounding tissue cells into the cuff 10 once the cuff 10 is positioned in an acceptable subcutaneous location and locked around a catheter inserted in an area to be catheterized. The fabric 12 may be any biocompatible fabric 12 suitable for promoting tissue ingrowth. Preferably, the fabric 12 is a tight-weave, low profile polyester such as, for example, a Dacron® composite. It should be understood by those of ordinary skill in the art from this disclosure that the fabric 12 to be used may be selected in accordance with such factors as the area of the body in which the cuff 10 is to be placed and patient tolerance to a particular fabric 12. It should also be understood that the cuff 10 may be attached to the surrounding tissue by methods other than use of a layer of fabric 12, such as, for example, suturing the device in the preferred location for securement.

As shown in FIGS. 1–3, the base 11 of the cuff 10 may comprise one or more ribs 56 on the interior surface 24 of the base 11. The ribs 56 extend radially inwardly into the passage 32. Once a catheter is inserted in the passage 32 and the cuff 10 is in the closed position as shown in FIG. 4, the ribs 56 function to provide slight pressure on the catheter 58 at the location of the ribs 56. The ribs 56 also preferably function to form a fluid seal and to prevent internal ingrowth of tissue which may cause fouling within the base 11. The ribs 56 may be of any geometric configuration including, for example, generally rounded, triangular or rectangular in cross section as long as the ribs 56 are sufficiently smooth such that the catheter 58 is not damaged or abraded. The ribs 56 may be located at any location throughout the length of the cuff 10. Preferably there is a rib 56 proximate each end of the passage 32 as shown in FIGS. 1 and 3 to form a fluid seal and prevent fouling. In addition, the ribs 56 preferably form a continuous annular ring on the interior surface 24 of the base 11 as shown in FIGS. 1–3. The ribs 56 may also take the form of a non-continuous ring or individual protrusions spaced at varying locations throughout the interior surface 24 of the base 11 resembling raised dots. While such designs provide a tightening function, they do not generally provide an adequate fluid seal.

In the preferred embodiment as shown in FIGS. 1–4, the base 11 of the cuff 10 also includes a third suture hole 46'. The third suture hole 46' is spaced longitudinally from the suture holes 46 located in the protruding sections 42, 44 of the arcuate members 13, 14.

Figure 7:
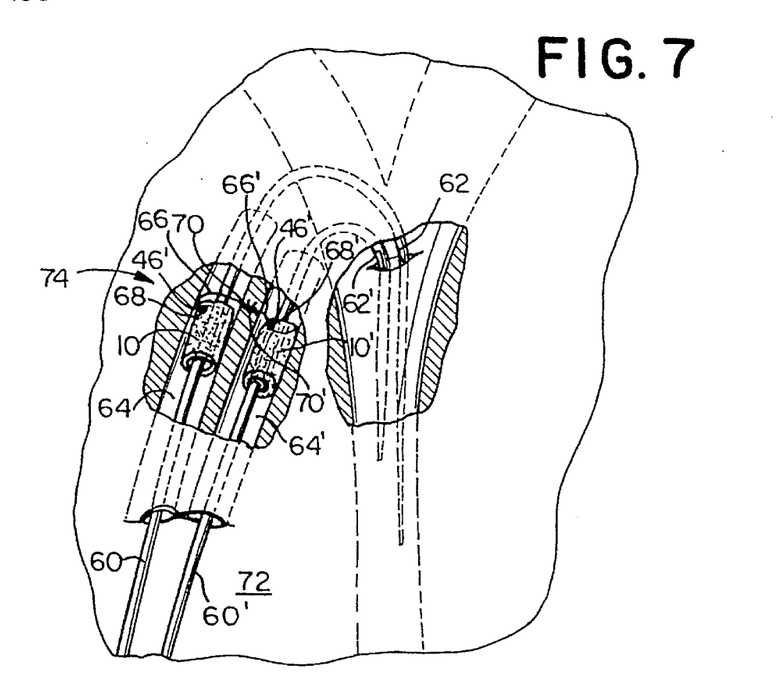
FIG. 7 is a diagrammatic view showing a preferred system for securing two catheters in two separate subcutaneous locations using two devices according to a preferred embodiment of the present invention.

As shown in FIG. 7, a catheter 60 is inserted in an area to be catheterized 62. A portion of the catheter 60 extending proximal to the area to be catheterized is inserted in the passage 32 of the base 11 of a cuff 10 having a third suture hole 46'. The cuff 10 is positioned in a desirable subcutaneous area 64 for securement. The base 11 is then locked in the closed position. A second piece of connecting material 66 is attached at one end 68 to the third suture hole 46'. The other end 70 of the connecting material 66 may be extended out of the body 72 enabling the cuff 10 to be fastened to any secure source providing additional stability to the catheter while it stabilizes within the area to be catheterized 62 or while tissue grows into the fabric 12.

A system of secured catheters 74 using the preferred cuff 10 is shown in FIG. 7. A second catheter 60' is inserted in a second area to be catheterized 62' and secured in a second subcutaneous area 64' by a second cuff 10' having a third suture hole. A further piece of the connecting material 66' is then fastened at one end 68' to the third suture hole of the cuff 10'. The other end 70' may be fastened to any secure source. As shown in FIG. 7, in a system of secured catheters 74 in accordance with the present invention, the ends 70, 70' are fastened to each other. After fastening the ends 70, 70' to each other, the connecting material 66, 66' is released by the physician and located internally such that there remains no external connecting material 66, 66' in such a system.

Preferably, connecting material 66 attached to the third suture hole 46' of a cuff 10 and fastened to a secure source, such as another connecting material 66', externally or internally, is a dissolvable connecting material 66. Any suitable dissolvable connecting material may be used. Preferably, the connecting material 66 is a dissolvable material such as an Epapbond braided dissolvable suture.

The connecting material 66 performs the function of providing additional stability to the cuff 10, while the cuff 10 and catheter stabilize in the subcutaneous location. Although any connecting material may be used, dissolvable suture material is preferred. Therefore, it is not necessary for the connecting material 66 to be permanent, especially since the connecting material 66 may be placed outside the body 72 of the patient where use of a non-dissolvable connecting material 66 may present a possibility of infection. In addition, while the material 66 may be permanent at a physician's discretion in a particular case, it is not preferred as it may increase the risk that bacteria may grow on the suture and spread into the patient causing infection.

The method for subcutaneous securement of a catheter in accordance with the present invention is performed using the cuff 10, as shown in FIGS. 1–3. The method includes the step of inserting a distal portion of a catheter into an area to be catheterized. The catheter may be any type known to those of ordinary skill in the art useful for draining or exchanging bodily fluids. Typical catheters include, for example, central venous and other intravenous catheters, shunts for drainage of bodily cavities, Tesio catheters, Swan-Ganz catheters and other similar devices.

The area to be catheterized may be any area in the body such as, for example, blood vessels, including the femoral, jugular and subclavian veins, any abscess cavity, post-operative cavity, the peritoneal cavity, and other areas of the body including intra-abdominal, sub-diaphragmatic and sub-hepatic areas. It should be understood by one of ordinary skill in the art from this disclosure that these areas are exemplary, and that the cuff 10 may be used to fasten any catheter or shunt inserted in various subcutaneous areas to be catheterized. FIG. 7 shows two central venous catheters 60, 60' inserted in two subcutaneous areas 62, 62' to be catheterized.

Once the distal portion of the catheter is within the area to be catheterized, cuff 10 is opened as shown in FIG. 3 such that a space 36 is created between the arcuate members 13, 14 for insertion of a portion of the catheter proximal the distal portion inserted in the area to be catheterized. Any portion of the catheter proximal the distal portion situated in the area to be catheterized may be inserted in the cuff 10, including portions of the cannula, hub area, extension tubes, or other related areas of the catheter proximal to the area to be catheterized. The proximal portion of the catheter is inserted in the space 36 such that it is positioned between the arcuate members 13, 14 The connecting material 48 should be between the proximal portion of the catheter and the interior surface 24 of the arcuate members 13, 14 of the cuff 10.

The cuff 10 is then moved by the physician along the proximal portion of the catheter until the cuff 10 is positioned in a stable area for securement. Areas for securement are determined by the physician depending upon the availability of tissue for attachment and ingrowth, effective alignment of the catheter within the subcutaneous area and ease of access to the area in which the catheter is to be secured. Many other factors, including the type of catheter, the part of the catheter to be secured, and the availability of subcutaneous area for securement will enter into the choice of a stable area. It should be understood that choice of a stable area will largely be a function of the physician's judgment in a particular medical situation.

Once an optimal area for securement is found, the physician stops moving the cuff 10 along the catheter and moves the arcuate members 13, 14 about the hinge 16 to the closed position such that the side surfaces 28, 30 are coupled in a facing relationship. If the cuff 10 does not lock by snapping the members 13, 14 closed, the physician then locks the cuff 10 manually by manipulating any locking device provided. As shown in FIG. 4, once the cuff 10 is locked, the catheter 58 is encircled in a tightened loop 54 of connecting material 48 and stabilized within the cuff 10. Preferably, fabric 12 covering the exterior surface 22 of the base 11 then promotes ingrowth of surrounding tissue cells into the cuff 10. Alternatively, the physician may then elect to suture or otherwise attach the cuff 10 to the surrounding tissue.

If the cuff 10 has a third suture hole 46', a second piece of connecting material 66 as shown in FIG. 7 is then fastened at one end 68 to the third suture hole 46' and may be drawn out through the body 72 through an opening created for insertion of the catheter 60 or through an opening made by a second incision if necessary. The second end 70 may also be left internally. In either case, the connecting material 66 is attached at the opposite end 70 to a secure source. The connecting material 66 may also be attached to the end 70' of a second piece of connecting material 66' attached to a second cuff 10' in a second subcutaneous location 64'. Once attached, the two pieces of attached connecting material 66, 66' are closed within the body 72.

The cuff 10 remains in place, and is removed with the catheter around which it has been positioned. The cuff 10 may then be discarded along with the catheter.

Figure 5:
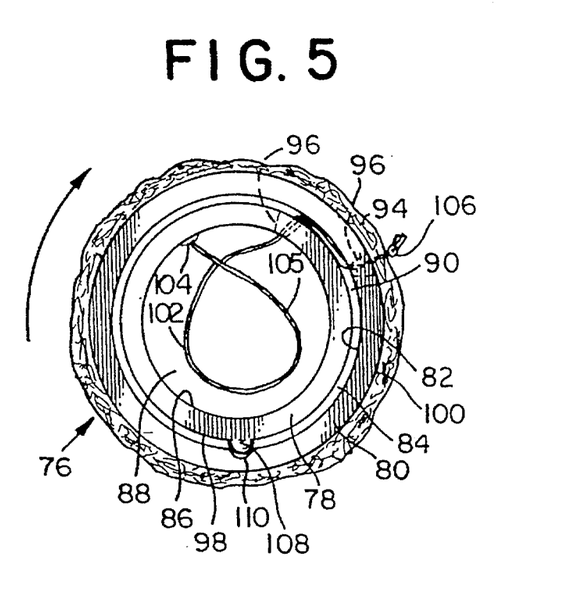
FIG. 5 is a front elevational view of an alternative preferred embodiment of a locatable device for subcutaneous securement of a catheter in an area to be catheterized according to the present invention.
Figure 6:
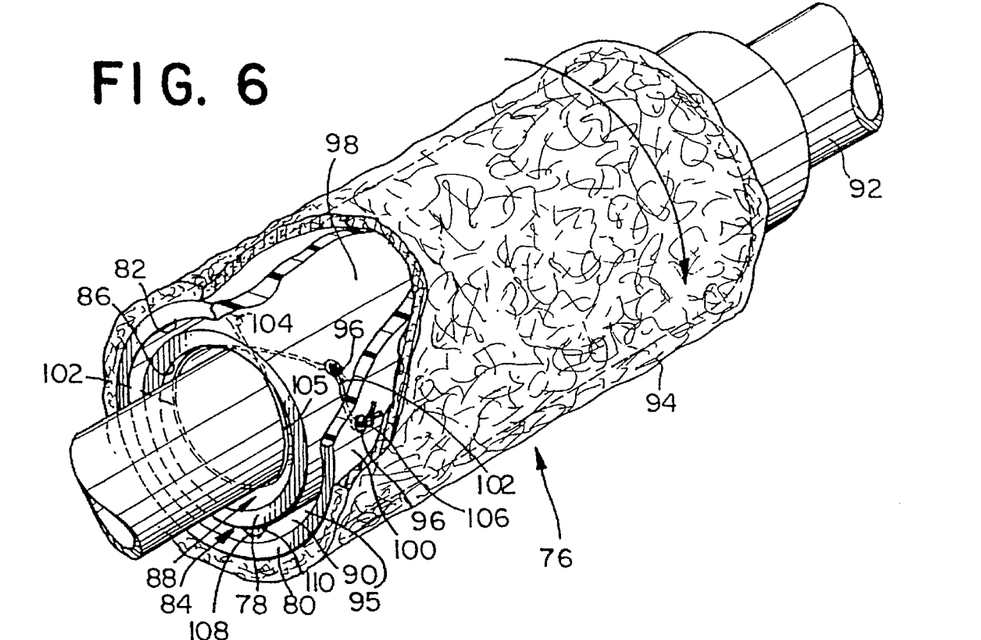
FIG. 6 is a perspective view of the device of FIG. 5 enclosed around a catheter.

An alternative embodiment of the cuff of the present invention is shown in FIGS. 5 and 6, and is generally indicated as 76. The cuff 76 includes first and second tubular members 78, 80. The tubular members 78, 80 may be manufactured from any of the biocompatible polymeric materials discussed above which are useful for manufacturing the arcuate members 13, 14 of the cuff 10. The tubular members 78, 80 preferably have a generally annular cross section, however, other cross sections such as, for example, elliptical, egg-shaped, oval, square and the like are within the scope of this invention. The second tubular member 80 has an interior surface 82 which defines a preferably generally cylindrical passage 84 extending longitudinally through the member 80. The first tubular member 78 has an interior surface 86 which also defines a preferably generally cylindrical passage 88 extending longitudinally through the first tubular member 78.

The second tubular member 80 has an inner diameter which is larger than the outer diameter of the first tubular member 78, and the first and second tubular members 78, 80 are positioned such that at least a portion of the first tubular member 78 lies within the passage 84. A space 90 is created between the first and second tubular members 78, 80 which is preferably generally annular.

While the first and second tubular members 78, 80 may have the same length, it is preferred that the tubular members 78, 80 be of different lengths to facilitate rotation of the cuff 76 by the physician once the cuff 76 is properly positioned. More preferably, the second tubular member 80 has a smaller length than the length of the first tubular member 78. When the first tubular member 78 is placed around a catheter 92 as shown in FIG. 6 its longer length allows the physician to grip the first tubular member 78 while rotating the second tubular member 80 around the first tubular member 78. The second tubular member 80, which is preferably covered by a layer of fabric 94 for ingrowth of surrounding tissue cells into the cuff 76 preferably has a wider diameter than the first member 78. It should be understood by one of ordinary skill in the art from this disclosure that the members 78, 80 may have varying or equivalent lengths without departing from the spirit of this invention.

Fabric 94 may be adhered to the tubular member 78 by any biocompatible medical grade adhesive known in the art such as those described above useful for attaching the fabric 12 to the base 11 of the cuff 10.

A hole 96, preferably a suture hole 96 is made through the first tubular member 78 and preferably through the second tubular member 80. Preferably, the suture holes 96 extend from the exterior surface 98, 100 to the interior surface 86, 82 of each member 78, 80. Preferably, the suture holes 96 are tapered as described above for the suture holes 46 in the cuff 10. Connecting material 102 made of the same material as the connecting material 48 is attached at one end 104 to the interior surface 86 of the tubular member 78. The end 104 may be fastened by any suitable means. For example, the end 104 may preferably be affixed to the interior surface 86 by a medical grade adhesive material. Alternatively, a second suture hole (not shown) may preferably be made in the first tubular member 78 and the end 104 may be knotted in the annular space 90 such that the connecting material 102 then extends down through the second suture hole into the passage 88.

The connecting material 102 is twisted to form a loop 105 of the material 102 within the passage 88. The second end 106 of the connecting material 102 is passed outwardly through the suture hole 96 in the tubular member 78 and either fastened to the second tubular member 80 by adhesive or preferably passed outwardly through a suture hole 96 in the second tubular member 80 such that it extends beyond the exterior surface 100 of the second tubular member 80. The end 106 is preferably knotted or adhered to the exterior surface 100 by adhesive. The connecting material 102 is positioned such that when a catheter 92 is placed within the loop 105 and the second tubular member 80 is rotated with respect to the first tubular member 78 as shown in FIG. 6, a portion of the connecting material 102 from the passage 88 is drawn through the space 90 and the loop 105 tightens around the catheter 92. The catheter 92 is thus secured within the passage 88. As discussed with respect to the cuff 10, the loop 105 should be tight enough to secure the catheter 92 within the passage 88, but not tight enough to constrict the catheter 92. Free flow of bodily fluid through the catheter 92 should be maintained. The loop 105 is preferably overlapping such that upon rotation of the first tubular member 78, the loop 54 tightens in a dynamic manner around the catheter 92.

The cuff 76, like the cuff 10 may include optional ribs as described above on the interior surface 86 of the first tubular member 78.

The cuff 76 preferably includes a locking device, such as, for example, an interlocking button 108 as shown in FIGS. 5 and 6. The button 108 is located on the exterior surface 98 of the first tubular member 78. The button 108 is movable in response to pressure until the cuff 76 has been rotated to tighten the loop 105. Once the cuff 76 has been rotated into position, the button snaps into a recessed mating hole 110 provided to the interior surface 82 of the second tubular member 80 to prevent further rotation of the cuff 76 thereby locking it into position. Alternatively, a latch or snap fitting for may be used to provide stability while the surrounding cells grow into the fabric 94.

An optional third suture hole spaced longitudinally from the suture holes 96 may be made in the first tubular member 78 of the cuff 76 such that the cuff 76 can be fastened to a secure source or used in a system for subcutaneously securing more than one catheter in an area to be catheterized as previously described with respect to the cuff 10.

An alternative preferred method for securement of a catheter in an area to be catheterized preferably uses the cuff 76. A distal portion of a catheter must be inserted in an area to be catheterized as described above using any suitable method. A loop 105 of connecting material 102 is formed in the passage 88 of a cuff 76 as shown in FIG. 5. A portion of the catheter proximal to the distal portion inserted in the area to be catheterized is inserted in the loop 105. The loop 105 and cuff 76 are moved along the catheter until the cuff 76 is situated in a preferred area for subcutaneous securement as described above.

Once the cuff is preferably situated, the first tubular member 80 is rotated with respect to the second tubular member 78 such that a portion of the connecting material 102 from within the passage 88 is pulled through the space 90 and the loop 105 is tightened around the catheter 92 thereby securing the catheter 92 within the passage 88 and maintaining free flow of bodily fluid through the catheter 92. Preferably, the cuff 76 is locked in place to prevent further rotation of the tubular members 78, 80. Preferably, fabric 94 adhered to the exterior surface 100 of the second tubular member 80 is allowed to promote ingrowth of surrounding tissue into the device for long term securement of the catheter. Alternatively, the physician may attach the cuff 76 to the surrounding tissue by any suitable method, such as, for example, suturing.

The cuff 76 is removed when the catheter is withdrawn from the body 72, and the cuff 76 is disposable along with the catheter.

Figure 8:
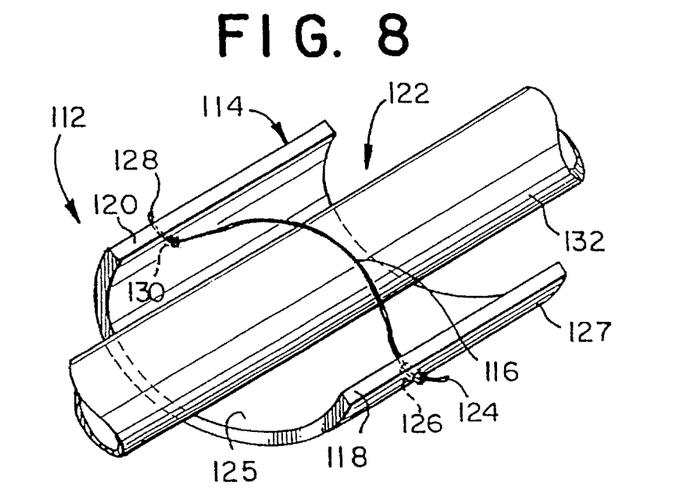
FIG. 8 is a perspective view of an alternative preferred embodiment of a locatable device for subcutaneous securement of a catheter in an area to be catheterized according to the present invention in an open position.
Figure 9:
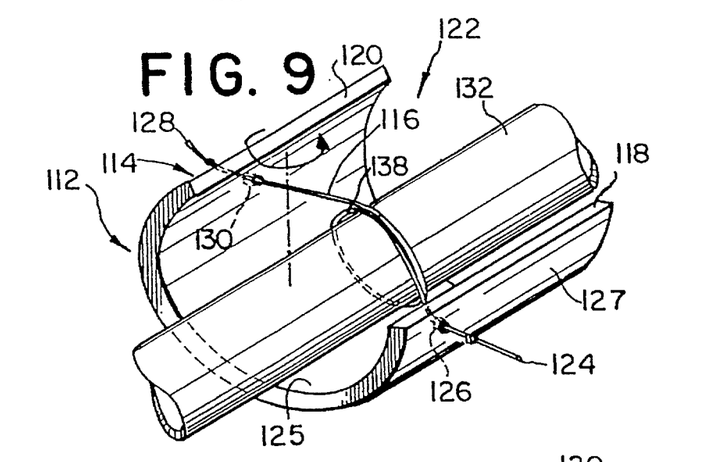
FIG. 9 is a perspective view of the device of FIG. 8 forming a loop around a catheter.
Figure 10:
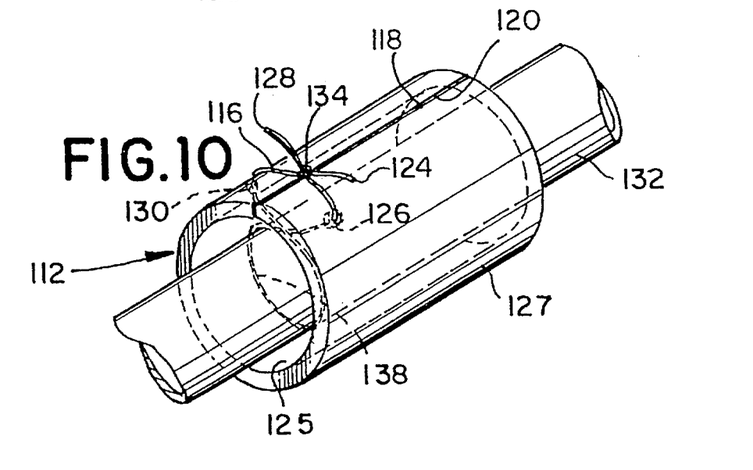
FIG. 10 is a perspective view of the device of FIG. 8 enclosed around a catheter.

An alternative embodiment of the cuff of the present invention is shown in FIGS. 8, 9 and 10, and is generally indicated as 112. The cuff is formed of an elastic base 114 and a connecting material 116.

The elastic base 114 may be moved from a flexed open position as shown in FIG. 8 to a relaxed closed position as shown in FIG. 10. The base 114 may be made of any flexible biocompatible thermoplastic polymer such as, for example, polypropylene, polyethylene and polyurethane. More preferably, the base 114 is formed from a preformed medical grade polypropylene such as the Class 6 biocompatible polypropylene described above with respect to the arcuate members 13, 14 of the cuff 10. However, the polypropylene base 114 should be preformed in the relaxed closed position to impart flexibility and elasticity to the base 114 such that when the base 114 is moved by application of manual force to the flexed open position, it returns to the relaxed closed position upon removal of the applied force. Any biocompatible polymer, such as those listed above as suitable for manufacture of the arcuate members 13, 14, may be used to manufacture the base 114; however, it will be understood by those of ordinary skill in the art that the polymeric material selected should be of sufficient flexibility such that it may be preformed to provide elastic movement to the base 114. Preferably, polymers having a high level of rigidity or stiffness upon molding are not used for forming the base 114.

Preferably, the base 114 is preformed and flexible such that in the relaxed position, it is in a closed tubular position as shown in FIG. 10 in which the first side surface 118 and the second opposite side surface 120 are proximate each other and a passage 121 for receiving a catheter is formed. Preferably, the side surfaces 118, 120 are in facing engagement when the base 114 is in the relaxed position. When the base 114 is flexed open, for example by manual force, the side surfaces 118, 120 are then separated from each other leaving a space 122 between them.

The connecting material 116 is preferably drawn at a first end 124 from the interior surface 125 of the base 114 through a first suture hole 126 spaced from the side surface 118 to the exterior surface 127. The second end 128 of the connecting material 116 is drawn from the interior surface 125 of the base 114 through a second suture hole 130 spaced from the side surface 120 to the exterior surface 127 of the base 114.

Preferably, when the ends 124, 128 of the material 116 are drawn through the suture holes 126, 130, the ends 124, 128 are knotted such that the connecting material does not pass back through the holes 126, 130.

The material 116 may also be connected to the interior surface 125 of the base 114, for example, by adhering the ends 124, 128 to the interior surface 125 of the base 114 with any acceptable medical grade adhesive such as those described above instead of drawing the ends 124, 128 through the suture holes 126, 130. If the ends 124, 128 are connected to the interior surface 125 of the base 114, the connecting material 116 must be of a length which would sufficiently tighten to assist in securing the catheter 132 within the cuff 112.

While the base is in the flexed open position as shown in FIG. 8, a portion of a catheter 132, proximal a distal portion (not shown) of the catheter 132 inserted in an area to be catheterized (not shown), may be inserted in the space 122 such that the portion of the catheter 132 is between the connecting material 116 and the interior surface 125 of the base 114.

At this point, the base 114 may be released from any application of force such that it returns to a relaxed position as shown in FIG. 10 and the catheter 132 is within the passage 121. The ends 124, 128 are then fastened together, preferably by tying the ends 124, 128 in a knot 134, such that the connecting material 116 forms at least a portion of a loop 138 which at least partially surrounds the catheter 132. Preferably the loop 138 is an overlapping loop as shown in FIGS. 9 and 10. An overlapping loop 138 is preferably formed by first rotating the base 114 with respect to the catheter 132 as shown in FIG. 9 about 180° prior to releasing the base 114 to return the base 114 to the relaxed position. An overlapping loop 138 provides a similar dynamic tightening function as the overlapping of the loops 54, 105 in the other embodiments of this invention. If the loop 138 is not overlapping, the suture holes 126, 130 should be spaced from the side surfaces 118, 120 such that when the ends 124, 128 are drawn together and fastened, the connecting material forms a partial loop 138 which effectively clamps the catheter 132 within the device (not shown).

When the ends 124, 128 are fastened, preferably forming an overlapping loop 138, the connecting material 116 is tightened around the catheter 132. The connecting material 116 should be drawn along the exterior surface 127 of the base 114 and the ends 124, 128 tied together such that the connecting material 116 is tight enough to secure the catheter 132 within the passage 121, but free flow of bodily fluid through the catheter 132 is maintained.

Like the cuff 10 and alternative cuff 76, the cuff 112 is also preferably covered with an outer layer of fabric (not shown) to promote ingrowth of surrounding tissue cells into the cuff 112. In addition, the cuff 112 may have an optional third suture hole (not shown) spaced longitudinally from the suture holes 132, 134 such that the cuff 112 can be fastened to a secure source or used in a system for subcutaneously securing more than one catheter in an area to be catheterized as previously described with respect to the cuffs 10, 76.

A further alternative method for securing a catheter in an area to be catheterized preferably uses the cuff 112. A distal portion of a catheter is inserted in an area to be catheterized in the manner shown in FIG. 7. The base 114 is moved to and maintained in the flexed open position as shown in FIG. 8. A portion of the catheter 132 proximal the distal end inserted in the area to be catheterized is inserted between the connecting material 116 and the base 114 as shown in FIG. 8. At least a portion of a loop 138 which at least partially surrounds the catheter 132 is then formed and the base 114 is then released such that it moves to the relaxed closed position. The first and second ends 124, 128 of the connecting material 116 are then fastened together, preferably by tying the ends 124, 128 into a knot 134 to tighten the connecting material 114 around the catheter 132 and to secure the catheter 132 within the base 114 while maintaining free flow of bodily fluid through the catheter 132.

Preferably, the base 114 is rotated with respect to the catheter 132 as shown in FIG. 9 about 180° prior to releasing the base 114 from the flexed open position such that the connecting material 116 forms an overlapping loop 138 around the catheter 132. The ends 124, 128 are then preferably tied together to secure the catheter 132 within the cuff 112.

In the preferred method, the catheter 132 is maintained securely within the cuff 112 until surrounding tissue cells grow into a fabric layer (not shown) adhered to the exterior surface 127 of the base 114. Alternatively, the cuff 112 may be held in place within the subcutaneous area to be secured by any suitable means as described above with respect to the cuff 10.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A locatable device for subcutaneous securement of a catheter in an area to be catheterized, comprising:

(a) a first tubular member having an exterior surface and an interior surface which defines a passage extending longitudinally through the first tubular member;

(b) a second tubular member having an exterior surface and an interior surface which defines a passage extending longitudinally through the second tubular member, at least a portion of the first tubular member being positioned within the passage of the second tubular member such that a space lies between the exterior surface of the first tubular member and the interior surface of the second tubular member;

(c) a hole in the first tubular member, the hole extending from the exterior surface to the interior surface;

(d) a connecting material fastened at a first end to the interior surface of the first tubular member and having a second end which passes outwardly through the hole and is fastened to the second tubular member, a length of the connecting material within the passage of the first tubular member being formed into a loop, whereby when a catheter is positioned within the loop the second tubular member is rotated with respect to the first tubular member to pull a portion of the length of the connecting material within the passage of the first tubular member into the space between the members and to tighten the loop around the catheter thereby securing the catheter within the passage of the first tubular member, the device maintaining free flow of bodily fluid through the catheter.

2. The device according to claim 1, further comprising fabric adhered to the exterior surface of the second tubular member for promoting ingrowth of surrounding tissue cells when the catheter is secured within the device.

3. The device according to claim 1, further comprising a hole in the second tubular member, the hole in the second tubular member extending from the exterior surface to the interior surface, wherein the second end of the connecting material passes outwardly through the hole in the first tubular member and through the hole in the second tubular member and is fastened to the exterior surface of the second tubular member.

4. The device according to claim 1, wherein the first and second tubular members have a length measured along a longitudinal axis of the device, the length of the second tubular member being less than the length of the first tubular member.

5. The device according to claim 1, wherein the device further comprises a lock.

* * * * *